(12) United States Patent
Gentry et al.

(10) Patent No.: US 7,304,152 B2
(45) Date of Patent: Dec. 4, 2007

(54) METRS2

(75) Inventors: Daniel R Gentry, King of Prussia, PA (US); David J Holmes, King of Prussia, PA (US); Karen A Ingraham, King of Prussia, PA (US)

(73) Assignee: Replidyne, Inc., Louisville, CO (US)

( * ) Notice: Subject to any disclaimer, the term of this patent is extended or adjusted under 35 U.S.C. 154(b) by 0 days.

(21) Appl. No.: 11/424,836

(22) Filed: Jun. 16, 2006

(65) Prior Publication Data

US 2007/0009993 A1 Jan. 11, 2007

Related U.S. Application Data

(60) Continuation of application No. 10/610,295, filed on Jun. 30, 2003, now Pat. No. 7,128,920, which is a division of application No. 10/444,611, filed on May 23, 2003, now abandoned, which is a continuation of application No. 10/243,291, filed on Sep. 13, 2002, now abandoned, which is a continuation of application No. 10/023,484, filed on Dec. 17, 2001, now abandoned, which is a continuation of application No. 09/966,728, filed on Sep. 28, 2001, now abandoned.

(60) Provisional application No. 60/236,104, filed on Sep. 28, 2000.

(51) Int. Cl.
*C07H 21/04* (2006.01)

(52) U.S. Cl. ............... 536/23.7; 435/69.1; 435/252.3; 435/320.1

(58) Field of Classification Search ............... 536/23.7; 435/320.1, 69.1, 252.3
See application file for complete search history.

(56) References Cited

OTHER PUBLICATIONS

Mikayama et al. (Nov. 1993. Proc.Natl.Acad.Sci. USA, vol. 90 : 10056-10060.*

Rudinger et al. (Jun. 1976. Peptide Hormones. Biol.Council. pp. 5-7).*

Altschul et al., (1990) Basic Local Alignment Search Tool. *J. Mol. Biol.*, 215: 403-410.

Chee et al., (1996) Accessing Genetic Information With High-Density DNA Arrays. *Science*, 274: 610-604.

Cotton et al., (1985) Reactivity of Cytosine and Thymine in Single-Base-Pair Mismatches with Hydroxylamine and Osmium Tetroxide and its Application to the Study of Mutations. *Proc. Natl. Acad. Sci.*, USA 85: 4397-4401.

Devereux et al., (1984) A Comprehensive Set of Sequence Analysis Programs for the VAX. *Nucleic Acids Research*, 12(1): 387-395.

Frohman et al., (1988) Rapid Production of Full-Length cDNAs from Rare Transcripts: Amplification Using a Single Gene-Specific Oligonucleotide Primer. *Proc. Natl. Acad. Sci.*, USA 85:8998-9002.

Gentz et al., (1989) Bioassay for Trans-Activation Using Purified Human Immunodeficiency Virus tat-Encoded Protein: Trans-Activation Requires mRNA Synthesis. *Proc. Natl. Acad. Sci.*, USA 86: 821-824.

Hentikoff and Hentikoff, (1992) Amino Acid Substitution Matrices from Protein Blocks. *Proc. Natl. Acad. Sci.*, USA 89: 10915-10919.

Needleman and Wunsch, (1970) A General Method Applicable to the Search for Similarities in the Amino Acid Sequence of Two Proteins. *J. Mol. Biol.*, 48: 443-453.

Rattan et al., (1992) Protein synthesis: Posttranslational Modifications and Aging. *Ann. N.Y. Acad. Sci.*, 663: 48-62.

Seifter et al., (1990) Analysis for Protein Modifications and Nonprotein Cofactors. *Meth. Enzymol.*, 182: 626-646.

* cited by examiner

*Primary Examiner*—Jennifer E. Graser
(74) *Attorney, Agent, or Firm*—Swanson & Bratschun, L.L.C.

(57) ABSTRACT

The invention provides metRS2 polypeptides and polynucleotides encoding metRS2 polypeptides and methods for producing such polypeptides by recombinant techniques. Also provided are preferred methods for utilizing metRS2 polypeptides and polynucleotides as diagnostic reagents and in diagnostic assays to screen for microbial infections in organisms and infections in materials.

4 Claims, No Drawings

METRS2

RELATED APPLICATIONS

This application is a continuation of U.S. application Ser. No. 10/610,295, filed on Jun. 30, 2003, now U.S. Pat. No. 7,128,920, which is a division of U.S. application Ser. No. 10/444,611, filed on May 23, 2003, now abandoned, which is a continuation of U.S. application Ser. No. 10,243,291, filed on Sep. 13, 2002, now abandoned, which is a continuation of U.S. application Ser. No. 10/023,484, filed on Dec. 17, 2001, now abandoned, which is a continuation of U.S. application Ser. No. 09/966,728, filed on Sep. 28, 2001, now abandoned, which claims benefit of U.S. Provisional Application No. 60/236,104, filed Sep. 28, 2000, the entire contents of which are incorporated by reference.

FIELD OF THE INVENTION

This invention relates to newly identified polynucleotides and polypeptides, and their production and uses, as well as their variants, and their uses. In particular, the invention relates to polynucleotides and polypeptides of the tRNA synthetase family, as well as their variants, herein referred to as "metRS2," "metRS2 polynucleotide(s)," and "metRS2 polypeptide(s)," as the case may be.

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ *Streptococcal* genes and gene products as targets for the development of antibiotics.

Infections caused by or related to *Streptococcus pneumoniae* are a major cause of human illness worldwide, and the frequency of resistance to standard antibiotics has risen dramatically over the last decade. Hence, there exists an unmet medical need for diagnostic tests and reagents for this organism.

Clearly, there exists a need for polynucleotides and polypeptides, such as the metRS2 embodiments of the invention that have a present benefit of, among other things, being useful to as diagnostic reagents. Such reagents are also useful to determine the frequency and geographical range of microbial strains.

SUMMARY OF THE INVENTION

The present invention relates to metRS2, in particular metRS2 polypeptides and metRS2 polynucleotides, recombinant materials and methods for their production. In another aspect, the invention relates to diagnostic assays and reagents for detecting diseases associated with microbial infections and conditions associated with such infections, such as assays and reagents for detecting metRS2 expression or activity, or the presence of *Streptococcus pneumoniae* in a host or material.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to metRS2 polypeptides and polynucleotides as described in greater detail elsewhere herein. In particular, the invention relates to polypeptides and polynucleotides of a metRS2 of *Streptococcus pneumoniae*, that is related by amino acid sequence homology to methionyl tRNA synthetase polypeptide. The invention relates especially to metRS2 having a nucleotide and amino acid sequences set out in Table 1 as SEQ ID NO:1 and SEQ ID NO:2 respectively. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1 metRS2 Polynucleotide and Polypeptide Sequences

A) *Streptococcus pneumoniae* metRS2 polynucleotide sequence [SEQ ID NO: 1].

5'-ATGTCAATTTTTATTGGAGGAGCATGGCCATATGCAAACGGTTCGTT

ACATATTGGTCACGCGGCAGCGCTTTTACCGGGGGATATTCTTGCAAGAT

ACTATCGTCAGAAGGGAGAGGAAGTTTTATATGTTTCTGGAAGTGATTGT

AATGGAACCCCTATTTCTATCAGAGCTAAAAAAGAAAATAAGTCTGTGAA

AGAAATTGCTGATTTTTATCATAAGGAATTTAAAGAAACTTTTGAAAAAT

TAGGTTTTACATATGACTTGTACTCGCGAACAGATTCTCCACTACATCAT

GAGATAGTACAAGAATTATTTTTGCAATTATACGAGAAGAAATTTTTGTA

TACAAAAAAATTAAACAACTCTATTGTACATTTGATAATCAATTCTTAC

CTGATAGGTTCGTTGAAGGAAAATGCCCGAATTGTGGAACCCATTCAAGA

GGAGATCAATGTGATAATTGCTCAGCAATTTTAGATCCTATAGATTTAGT

TGATAAAAGATGTTCTATTTGTTCCAATGAACCAGAAGTTCGTGAGACAG

AACACTTTTATTATGTTTTTAGTGAGTTTCAAAATTTGTTAGAGACTTAC

TTAAATGATGCTGAAGAAACAGTGAGATGGCGAAAAAATGCAATAAATCT

AACTAAAAGGTATTTACGGGAAGGTTTACCTGATCGAGCTGTTACTCGTG

ATCTACCAAATGGGATTCCAGTTCCCATTGATGGTTTTAGAGATAAAAAA

ATATATGTCTGGTTTGAAGCGGTAGCAGGTTACTACACAGCAAGTGTTGA

TTGGGCGCAAAAACTTCAAAATAATATTACTGATTTTTGGAACAATCGGA

CAAAGTCATATTATGTTCATGGAAAAGATAACATCCCATTTCATACTATT

ATTTGGCCGGCAATACTCTCAGGTTTAGAAATAGAGCCTCTTCCAGAGTA

TATTATTTCTAGTGAATATTTAACGTTAGAAAACAAAAAAATATCAACAA

GTAATAATTGGGCTATATGGCTTAACGATATCATAAAAAAATATGATGCT

GATTCAATCCGATACTTCCTAACAATAAATGCTCCTGAGATGAAAGATGC

TABLE 1-continued metRS2 Polynucleotide and Polypeptide Sequences

AAATTTTTCTTGGAGAGAATTTATTTATAGTCATAACTCAGAATTATTAG

GATCGTACGGTAATTTTATCAATAGGACTCTAAAGTTTATTGAAAAGTAT

TTTGAATCTGAAATACCCACTAAATATCTCGAAGGAGAAATTTTATATAA

TTTGAAAGAATTATATACAACAGTAGGTAATTTAGTTGAGAGCGGGCATA

TGAAACAGGCATTAGAAGAAATTTTTGAATATATTAGATCGGCTAATAAA

TTCTATGATGATATGAAACCGTGGGCATTGCGAGAGTCCGATATTGAAAA

ATGTAAAGAAGTCTTAGCTACTTGTGTAATCATTATACTTAATTTAGGAC

AAATGTTAAATCCATTCATTCCTTTTTCTGGTAAAAAGATTGAGGATATG

TTTAAAACAAAGCTAAATACTTGGAATTATATTTCAAACCTTCCTAACAA

GCTATCAGATGTATCAATGTTGTTTGATAGGATTGATTTGAAAAAAATTG

ACGAGGAAGTTTTAGAATTGCAACAAACATCCAGTAGATAA-3'

(B) *Streptococcus pneumoniae* metRS2 polypeptide sequence deduced from a polynucleotide sequence in this table [SEQ ID NO:2].

NH₂-MSIFIGGAWPYANGSLHIGHAAALLPGDILARYYRQKGEEVLYVSG

SDCNGTPISIRAKKENKSVKEIADFYHKEFKETFEKLGFTYDLYSRTDSP

LHHEIVQELFLQLYEKKFLYTKKIKQLYCTFDNQFLPDRFVEGKCPNCGT

HSRGDQCDNCSAILDPIDLVDKRCSICSNEPEVRETEHFYYVFSEFQNLL

ETYLNDAEETVRWRKNAINLTKRYLREGLPDRAVTRDLPNGIPVPIDGFR

DKKIYVWFEAVAGYYTASVDWAQKLQNNITDFWNNRTKSYYVHGKDNIPF

HTIIWPAILSGLEIEPLPEYIISSEYLTLENKKISTSNNWAIWLNDIIKK

YDADSIRYFLTINAPEMKDANFSWREFIYSHNSELLGSYGNFINRTLKFI

EKYFESEIPTKYLEGEILYNLKELYTTVGNLVESGHMKQALEEIFEYIRS

ANKFYDDMKPWALRESDIEKCKEVLATCVIIILNLGQMLNPFIPFSGKKI

EDMFKTKLNTWNYISNLPNKLSDVSMLFDRIDLKKIDEEVLELQQTSSR-COOH

Deposited Materials

A deposit comprising a *Streptococcus pneumoniae* strain has been deposited with the National Collections of Industrial and Marine Bacteria Ltd. (herein "NCIMB"), 23 St. Machar Drive, Aberdeen AB2 1RY, Scotland on 11 Apr. 1996 and assigned deposit number 40794. The deposit was described as *Streptococcus pneumoniae* 0100993 on deposit.

On 17 Apr. 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain comprises a full length metRS2 gene. The sequence of the polynucleotides comprised in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule encoding a mature polypeptide expressible by the *Streptococcus pneumoniae* strain, which polypeptide is comprised in the deposited strain. Further provided by the invention are metRS2 polynucleotide sequences in the deposited strain, such as DNA and RNA, and amino acid sequences encoded thereby. Also provided by the invention are metRS2 polypeptide and polynucleotide sequences isolated from the deposited stain.

Polypeptides

MetRS2 polypeptide of the invention is substantially phylogenetically related to other proteins of the tRNA synthetase family.

In one aspect of the invention there are provided polypeptides of *Streptococcus pneumoniae* referred to herein as "metRS2" and "metRS2 polypeptides" as well as biologically, diagnostically and clinically useful variants thereof, and compositions comprising the same.

Among the particularly preferred embodiments of the invention are variants of metRS2 polypeptide encoded by naturally occurring alleles of a metRS2 gene.

The present invention further provides for an isolated polypeptide that: (a) comprises or consists of an amino acid sequence that has at least 95% identity, most preferably at least 97-99% or exact identity, to that of SEQ ID NO:2 over the entire length of SEQ ID NO:2; (b) a polypeptide encoded by an isolated polynucleotide comprising or consisting of a polynucleotide sequence that has at least 95% identity, even more preferably at least 97-99% or exact identity to SEQ ID NO:1 over the entire length of SEQ ID NO:1, or the entire length of that portion of SEQ ID NO:1 which encodes SEQ ID NO:2; (c) a polypeptide encoded by an isolated polynucleotide comprising or consisting of a polynucleotide sequence encoding a polypeptide that has at least 95% identity, even more preferably at least 97-99% or exact identity, to the amino acid sequence of SEQ ID NO:2, over the entire length of SEQ ID NO:2.

The polypeptides of the invention include a polypeptide of Table 1 [SEQ ID NO:2] (in particular a mature polypeptide) as well as polypeptides and fragments, particularly those that are useful as diagnostic reagents, as well as those that have at least 95% identity to a polypeptide of Table 1 [SEQ ID NO:2]. Also included by the invention are portions of such polypeptides generally comprising at least 30 amino acids, and more preferably comprising at least 50 amino acids.

The invention also includes a polypeptide consisting of or comprising a polypeptide of the formula:

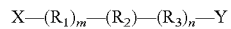

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from *Streptococcus pneumoniae*, however, it may preferably be obtained from other organisms of the same taxonomic genus. A polypeptide of the invention may also be obtained, for example, from organisms of the same taxonomic family or order, among others.

A fragment is a variant polypeptide having an amino acid sequence that is entirely the same as part but not all of any amino acid sequence of any polypeptide of the invention. MetRS2 polypeptide fragments may be "free-standing" or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2], or of variants thereof, such as a continuous series of residues that includes an amino- and/or carboxyl-terminal amino acid sequence. Degradation forms of the polypeptides of the invention produced by or in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and substrate binding regions.

Further preferred fragments include an isolated polypeptide comprising an amino acid sequence having at least 15, 20, 30, 40, 50 or 100 contiguous amino acids from the amino acid sequence of SEQ ID NO:2, or an isolated polypeptide comprising an amino acid sequence having at least 15, 20, 30, 40, 50 or 100 contiguous amino acids truncated or deleted from the amino acid sequence of SEQ ID NO:2.

Fragments of the polypeptides of the invention may be employed for producing the corresponding full-length polypeptide by peptide synthesis; therefore, these variants may be employed as intermediates for producing the full-length polypeptides of the invention.

Polynucleotides

It is an object of the invention to provide polynucleotides that encode metRS2 polypeptides.

In a particularly preferred embodiment of the invention the polynucleotide comprises a region encoding metRS2 polypeptides comprising a sequence set out in Table 1 [SEQ ID NO:1], including a full length gene, or a variant thereof. This invention further provides that this full length gene is essential to the growth and survival of an organism that possesses it, such as *Streptococcus pneumoniae*.

As a further aspect of the invention there are provided isolated polynucleotides encoding and/or expressing metRS2 polypeptides and polynucleotides, particularly *Streptococcus pneumoniae* metRS2 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically or clinically useful polynucleotides and polypeptides, and variants thereof, and compositions comprising the same.

Another aspect of the invention relates to isolated polynucleotides, including at least one full length gene, that encodes a metRS2 polypeptide having a deduced amino acid sequence of Table 1 [SEQ ID NO:2], and polynucleotides closely related thereto, as well as variants thereof.

In another particularly preferred embodiment of the invention there is a metRS2 polypeptide from *Streptococcus pneumoniae* comprising or consisting of an amino acid sequence of Table 1 [SEQ ID NO:2], or a variant thereof.

Using the information provided herein, such as a polynucleotide sequence set out in Table 1 [SEQ ID NO:1], a polynucleotide of the invention encoding metRS2 polypeptide may be obtained using standard cloning and screening methods, such as those for cloning and sequencing chromosomal DNA fragments from bacteria using *Streptococcus pneumoniae* cells as stating material, followed by obtaining a full length clone. For example, to obtain a polynucleotide sequence of the invention, such as a polynucleotide sequence given in Table 1 [SEQ ID NO:1], typically a library of clones of chromosomal DNA of *Streptococcus pneumoniae* in *E. coli*, or some other suitable host, is probed with a radiolabeled oligonucleotide, preferably a 17-mer or longer, derived from a sequence fragment of the invention. Clones carrying DNA identical to that of the probe can then be distinguished using stringent hybridization conditions. By sequencing the individual clones thus identified by hybridization with sequencing primers designed from the original polypeptide or polynucleotide sequence, it is then possible to extend the polynucleotide sequence in both directions to determine a full length gene sequence. Conveniently, such sequencing is performed, for example, using denatured double-stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (See in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in Table 1 [SEQ ID NO:1] was discovered in a DNA library derived from *Streptococcus pneumoniae*.

Moreover, each DNA sequence set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known to those skilled in the art. The polynucleotide of SEQ ID NO:1, between nucleotide number ATG and the stop codon that begins at nucleotide number TAA of SEQ ID NO:1, encodes the polypeptide of SEQ ID NO:2.

In a further aspect, the present invention provides for an isolated polynucleotide comprising or consisting of: (a) a polynucleotide sequence that has at least 95% identity, even more preferably at least 97%, still more preferably 98% and yet still more preferably 99% identity, or exact identity to SEQ ID NO:1 over the entire length of SEQ ID NO:1, or the entire length of that portion of SEQ ID NO:1 which encodes SEQ ID NO:2; (b) a polynucleotide sequence encoding a polypeptide that has at least 95% identity, even more preferably at least 97%, still more preferably 98% and yet still more preferably 99% identity, or 100% exact, to the amino acid sequence of SEQ ID NO:2, over the entire length of SEQ ID NO:2.

A polynucleotide encoding a polypeptide of the present invention, including homologs and orthologs from species other than *Streptococcus pneumoniae*, may be obtained by a process that comprises the steps of screening an appropriate library under stringent hybridization conditions with a labeled or detectable probe consisting of or comprising the sequence of SEQ ID NO:1 or a fragment thereof; and isolating a full length gene and/or genomic clones comprising said polynucleotide sequence.

The invention provides a polynucleotide sequence identical over its entire length, to a coding sequence (open reading frame) in Table 1 [SEQ ID NO:1]. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also comprise at least one non-coding sequence, including for example, but not limited to at least one noncoding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of a fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of that may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide ATG to the nucleotide immediately upstream of or including nucleotide TAA set forth in SEQ ID NO:1 of Table 1, both of that encode a metRS2 polypeptide.

The invention also includes a polynucleotide consisting of or comprising a polynucleotide of the formula:

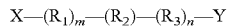

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, that can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Streptococcus pneumoniae*, however, it may preferably be obtained from other organisms of the same taxonomic genus. A polynucleotide of the invention may also be obtained, for example, from organisms of the same taxonomic family or order, among others.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* metRS2 having an amino acid sequence set out in Table 1 [SEQ ID NO:2]. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may comprise coding and/or non-coding sequences.

The invention further relates to variants of the polynucleotides described herein that encode variants of a polypeptide having a deduced amino acid sequence of Table 1 [SEQ ID NO:2]. Fragments of polynucleotides of the invention may be used, for example, to synthesize full length polynucleotides of the invention.

Further particularly preferred embodiments are polynucleotides encoding metRS2 variants, that have the amino acid sequence of metRS2 polypeptide of Table 1 [SEQ ID NO:2] in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties or activities of metRS2 polypeptide.

Preferred isolated polynucleotide embodiments also include polynucleotide fragments, such as a polynucleotide comprising a nucleic acid sequence having at least 15, 20, 30, 40, 50 or 100 contiguous nucleic acids from the polynucleotide sequence of SEQ ID NO:1, or an polynucleotide comprising a nucleic acid sequence having at least 15, 20, 30, 40, 50 or 100 contiguous nucleic acids truncated or deleted from the 5' and/or 3' end of the polynucleotide sequence of SEQ ID NO:1.

Further preferred embodiments of the invention are polynucleotides that are at least 95% or 97% identical over their entire length to a polynucleotide encoding metRS2 polypeptide having an amino acid sequence set out in Table 1 [SEQ ID NO:2], and polynucleotides that are complementary to such polynucleotides. Most highly preferred are polynucleotides that comprise a region that is at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as a mature polypeptide encoded by a DNA of Table 1 [SEQ ID NO:1].

In accordance with certain preferred embodiments of this invention there are provided polynucleotides that hybridize, particularly under stringent conditions, to metRS2 polynucleotide sequences, such as those polynucleotides in Table 1.

The invention further relates to polynucleotides that hybridize to the polynucleotide sequences provided herein. In this regard, the invention especially relates to polynucleotides that hybridize under stringent conditions to the polynucleotides described herein. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library comprising a complete gene for a polynucleotide sequence set forth in SEQ ID NO:1 under stringent hybridization conditions with a probe having the sequence of said polynucleotide sequence set forth in SEQ ID NO:1 or a fragment thereof, and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding metRS2 and to isolate cDNA and genomic clones of other genes that have a high identity, particularly high sequence identity, to a metRS2 gene. It is preferred that these probes be used in the diagnostic embodiments provided herein. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a metRS2 gene may be isolated by screening using a DNA sequence provided in Table 1 [SEQ ID NO:1] to synthesize an oligonucleotide probe. A labeled oligonucleotide having a sequence complementary to that of a gene of the invention is then used to screen a library of cDNA, genomic DNA or mRNA to determine to which members of the library the probe hybridizes.

There are several methods available and well known to those skilled in the art to obtain full length DNAs, or extend short DNAs, for example those based on the method of Rapid Amplification of cDNA ends (RACE) (see, for example, Frohman, et al., PNAS USA 85: 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full length DNA constructed either by joining the product directly to the existing DNA to give a complete sequence, or carrying out a separate full length PCR using the new sequence information for the design of the 5' primer.

The polynucleotides and polypeptides of the invention may be employed, for example, as research reagents and materials for discovery of diagnostics for diseases, particularly human diseases, as further discussed herein relating to polynucleotide assays.

The polynucleotides of the invention that are oligonucleotides derived from a sequence of Table 1 [SEQ ID NOS:1 or 2] may be used in the processes herein as described, but preferably for PCR, to determine whether or not the polynucleotides identified herein in whole or in part are transcribed in bacteria in infected tissue or bodily fluids. It is recognized that such sequences will also have utility in diagnosis of the stage of infection and type of infection the pathogen has attained.

The invention also provides polynucleotides that encode a polypeptide that is a mature protein plus additional amino or carboxyl-terminal amino acids, or amino acids interior to a mature polypeptide (when a mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from a mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

As will be recognized, the entire polypeptide encoded by an open reading frame is often not required for activity. Accordingly, it has become routine in molecular biology to map the boundaries of the primary structure required for activity with N-terminal and C-terminal deletion experiments. These experiments utilize exonuclease digestion or convenient restriction sites to cleave coding nucleic acid sequence. For example, Promega (Madison, Wis.) sell an Erase-a-base™ system that uses Exonuclease III designed to facilitate analysis of the deletion products (protocol is known in the art and available from Promega (Madison, Wis.)). The digested endpoints can be repaired (e.g., by ligation to synthetic linkers) to the extent necessary to preserve an open reading frame. In this way, the nucleic acid of SEQ ID NO:1 readily provides contiguous fragments of SEQ ID NO:2 sufficient to provide an activity, such as an enzymatic, binding or antibody-inducing activity. Nucleic acid sequences encoding such fragments of SEQ ID NO:2 and variants thereof, as described herein, are within the scope of the invention, as are polypeptides so encoded.

As is known in the art that portions of the N-terminal and/or C-terminal sequence of a protein can generally be removed without serious consequence to the function of the protein. The amount of sequence that can be removed is often quite substantial. The nucleic acid cutting and deletion methods used for creating such deletion variants are now quite routine. Accordingly, any contiguous fragment of SEQ ID NO:2 which retains at least 20%, preferably at least 50%, of an activity of the polypeptide encoded by the gene for SEQ ID NO:2 is within the invention, as are corresponding fragment which are 70%, 80%, 90%, 95%, 97%, 98% or 99% identical to such contiguous fragments. In one embodiment, the contiguous fragment comprises at least 70% of the amino acid residues of SEQ ID NO:2, preferably at least 80%, 90% or 95% of the residues.

In sum, a polynucleotide of the invention may encode a mature protein, a mature protein plus a leader sequence (that may be referred to as a preprotein), a precursor of a mature protein having one or more prosequences that are not the leader sequences of a preprotein, or a preproprotein, that is a precursor to a proprotein, having a leader sequence and one or more prosequences, that generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells that are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-Dexan mediate transfection, transvection, microinjection, cationic lipid-mediated transfection, electroporation, transduction, scrape loading, ballistic introduction and infection.

Representative examples of appropriate hosts include bacterial cells, such as cells of *streptococci, staphylococci, enterococci E. coli, streptomyces, cyanobacteria, Bacillus subtilis*, and *Streptococcus pneumoniae*; fungal cells, such as cells of a yeast, *Kluveromyces, Saccharomyces*, a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosoial-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs may comprise control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of metRS2 polynucleotides and polypeptides of the invention for use as diagnostic reagents. Detection of mRS2 polynucleotides and/or polypeptides in a eukaryote, particularly a mammal, and especially a human, will provide a diagnostic method for diagnosis of disease or staging of disease. Eukaryotes, particularly mammals, and especially humans, particularly those infected or suspected to be infected with an organism comprising the metRS2 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled metRS2 polynucleotide sequences. Perfectly or significantly matched sequences can be distinguished from imperfectly or more significantly matched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science,* 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA,* 85: 4397-4401 (1985).

In another embodiment an array of oligonucleotides probes comprising metRS2 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science,* 274: 610 (1996)).

In another aspect, the present invention relates to a diagnostic kit that comprises: (a) a polynucleotide of the present invention, preferably the nucleotide sequence of SEQ ID NO:1, or a fragment thereof; (b) a nucleotide sequence complementary to that of (a); (c) a polypeptide of the present invention, preferably the polypeptide of SEQ ID NO:2 or a fragment thereof, or (d) an antibody to a polypeptide of the present invention, preferably to the polypeptide of SEQ ID NO:2. It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferably, SEQ ID NO:1, that is associated with a disease or pathogenicity will provide a diagnostic tool that can add to, or define, a diagnosis of a disease, a prognosis of a course of disease, a determination of a stage of disease, or a susceptibility to a disease, that results from or is associated with expression, particularly under-expression, over-expression or altered expression, of a polynucleotide of the invention. Organisms, particularly infectious organisms, carrying mutations in such polynucleotide may be detected at the polynucleotide level by a variety of techniques, such as those described elsewhere herein.

The differences in a polynucleotide and/or polypeptide sequence between organisms possessing a first phenotype and organisms possessing a different, second different phenotype can also be determined. If a mutation is observed in some or all organisms possessing a first phenotype but not in any organisms possessing a second phenotype, then the mutation is likely to be a causative or associated agent of the first phenotype.

Cells from an organism carrying mutations or polymorphisms (allelic variations) in a polynucleotide and/or polypeptide of the invention may also be detected at the polynucleotide or polypeptide level by a variety of techniques, to allow for serotyping, among other things. For example, RT-PCR can be used to detect mutations in the RNA. It is particularly preferred to use RT-PCR in conjunction with automated detection Systems, such as, for example, GeneScan. RNA, cDNA or genomic DNA may also be used for the same purpose. As a further example, PCR primers complementary to a polynucleotide encoding metRS2 polypeptide can be used to identify and analyze mutations. The invention further provides these primers with 1, 2, 3 or 4 nucleotides removed from the 5' and/or the 3' end. These primers may be used for, among other things, amplifying metRS2 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Streptococcus pneumoniae*, comprising determining from a sample derived from an individual, such as a bodily material, a polynucleotide having a sequence set forth in Table 1 [SEQ ID NO:1]. Moreover, increased or decreased expression of a metRS2 polynucleotide can be used as a diagnostic, and be measured using any one of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of metRS2 polypeptide compared to normal control tissue samples (usually showing no such expression) may be used to detect the presence of an infection, for example. Assay techniques that can be used to determine levels of a metRS2 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

GLOSSARY

The following definitions are provided to facilitate understanding of certain terms used frequently herein.

"Bodily material(s) means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

"Disease(s)" means any disease caused by or associated with infection by an organism, including, for example, otitis media, conjunctivitis, pneumonia, bacteremia, meningitis, sinusitis, pleural empyema and endocarditis, and most particularly meningitis, such as for example infection of cerebrospinal fluid.

"Host cell(s)" is a cell that has been introduced (e.g., transformed or transfected) or is capable of introduction (e.g., transformation or transfection) by an exogenous polynucleotide sequence.

"Identity," as known in the art is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990). The BLAST X program is publicly available from NCBI and other sources (*BLAST Manual*, Altschul, S., et al., NCBI NLM NIH Bethesda, Md. 20894; Altschul, S., et al, *J. Mol. Biol.* 215: 403-410 (1990). The well known Smith Waterman algorithm may also be used to determine identity.

Parameters for polypeptide sequence comparison include the following: Algorithm: Needleman and Wunsch, J. Mol. Biol. 48: 443-453 (1970)

Comparison matrix: BLOSSUM62 from Hentikoff and Hentikoff, Proc. Natl. Acad. Sci. USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol. Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Individual(s)" means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetelia, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Closhidium perfringens, Clostridium tetani, Clostridium botulinum, Treponema pallidum, Rickettsia rickettsii, Helicobacter pylori* and *Chlamydia trachomitis*, (ii) an archaeon, including but not limited to *Archaebacter*, and (iii) a unicellular or filamentous eukaryote, including but not limited to, a protozoan, a fungus, a member of the genus *Saccharomyces, Kluveromyces*, or *Candida*, and a member of the species *Saccharomyces ceriviseae, Kluveromyces lactis*, or *Candida albicans*.

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1-12 in *POSTTRANSLATIONAL COVA-*

LENT MODIFICATION OF PROTEINS, B: C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile, among Ser and Thr, among the acidic residues Asp and Glu; among Asn and Glu; and among the basic residues Lys and Arg; or aromatic residues Phe and Tyr. Particularly preferred are variants in which several, 5-10, 1-5, 1-3, 1-2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, that are well known and routine to those of skill in the art, except where otherwise described in detail. The examples are illustrative, but do not limit the invention.

Example 1

Strain Selection, Library Production and Sequencing

The gene of SEQ ID NO:1 was cloned by its ability to confer resistance to a sensitive strain of *S. pneumoniae*. Further, the strain used for the complementation was a resistant strain, QA1442, which was made sensitive by mutagenesis, prior to cloning and sequencing the clone of SEQ ID NO:1. A QA1442 library was used to allow it to regain resistance. The resulting clones did confer resistance to the strain R6 which is normally sensitive; thus, the invention of the sequence of SEQ ID NO:1 was made.

The gene has been detected in at least two strains of *S. pneumoniae* that are resistant to methionyl tRNA synthetase inhibitors. It is estimated that this gene is present in about 20% of all *S. pneumoniae* strains based on the distribution of resistance to methionyl tRNA synthetase inhibitors among *S. pneumoniae* isolates.

The invention claimed is:

1. An isolated polynucleotide selected from the group consisting of:
   (i) an isolated polynucleotide comprising a polynucleotide sequence encoding a polypeptide that has at least 95% identity to the amino acid sequence of SEQ ID NO:2, over the entire length of SEQ ID NO:2;
   (ii) an isolated polynucleotide comprising a polynucleotide sequence that has at least 95% identity over its entire length to a polynucleotide sequence encoding the polypeptide of SEQ ID NO:2;
   (iii) an isolated polynucleotide comprising a nucleotide sequence that has at least 95% identity to that of SEQ ID NO:1 over the entire length of SEQ ID NO: 1;
   (iv) an isolated polynucleotide comprising a nucleotide sequence, which encodes the polypeptide of SEQ ID NO:2;
   (v) an isolated polynucleotide consisting of the nucleic acid sequence set forth in SEQ ID NO: 1;
   (vi) an isolated polynucleotide of at least 30 nucleotides in length obtainable by screening an appropriate library comprising a gene for a polynucleotide represented by SEQ ID NO: 1 under stringent hybridization conditions with a probe having the sequence of SEQ ID NO:1 or a fragment thereof of at least 30 nucleotides in length, wherein the hybridization conditions comprise overnight incubation at about 42° C. in a solution comprising about 50% formamide, about 5×SSC, about 50 mM sodium phosphate, about 5× Denhardt's solution, about 10% dextran sulfate, and about 20 µg/ml salmon sperm DNA, followed by washing with about 0.1×SSC at about 65° C.;
   (vii) an isolated polynucleotide having at least 95% identity to the polynucleotide represented by SEQ ID NO: 1 encoding a mature polypeptide expressed by the metRS2 gene comprised in *Streptococcus pneumoniae;* and
   (viii) a polynucleotide sequence fully complementary to said isolated polynucleotide of (i), (ii), (iii), (iv), (v), (vi), or (vii);
   wherein the polynucleotide encodes for a polypeptide which functions to confer resistance to methionyl tRNA synthetase inhibitors.

2. A process for producing a polypeptide selected from the group consisting of:
   (i) an isolated polypeptide comprising an amino acid sequence selected from the group having at least 95% identity to the amino acid sequence of SEQ ID NO:2 over the entire length of SEQ ID NO:2,
   wherein said polypeptide functions to confer resistance to methionyl tRNA synthetase inhibitors;
   (ii) an isolated polypeptide comprising the amino acid sequence of SEQ ID NO:2; (iii) an isolated polypeptide consisting of the amino acid sequence set forth in SEQ ID NO:2; and
   (iii) a polypeptide that is encoded by a recombinant polynucleotide comprising the polynucleotide sequence of SEQ ID NO:1, comprising culturing a host cell under conditions sufficient for the production of the polypeptide,
   wherein the host cell comprises an expression system having a nucleic acid encoding the polypeptide of (i), (ii), or (iii).

3. A process for producing a host cell comprising an expression system or a membrane thereof expressing a polypeptide selected from the group consisting of:
   (i) an isolated polypeptide comprising an amino acid sequence selected from the group having at least 95% identity to the amino acid sequence of SEQ ID NO:2 over the entire length of SEQ ID NO:2,
   wherein said polypeptide functions to confer resistance to methionyl tRNA synthetase inhibitors;
   (ii) an isolated polypeptide comprising the amino acid sequence of SEQ ID NO:2;
   (iii) an isolated polypeptide consisting of the amino acid sequence set forth in SEQ ID NO:2; and
   (iv) a polypeptide that is encoded by a recombinant polynucleotide comprising the polynucleotide sequence of SEQ ID NO:1,
   said process comprising transforming or transfecting a cell with an expression system comprising a polynucleotide capable of producing said polypeptide of (i), (ii), (iii) or (iv) when said expression system is present in a compatible host cell such that the host cell, under appropriate culture conditions, produces said polypeptide of (i), (ii), (iii) or (iv).

4. A host cell expressing a polypeptide selected from the group consisting of:
   (i) an isolated polypeptide comprising an amino acid sequence selected from the group having at least 95% identity to the amino acid sequence of SEQ ID NO:2 over the entire length of SEQ ID NO:2,
   wherein said polypeptide functions to confer resistance to methionyl tRNA synthetase inhibitors;
   (ii) an isolated polypeptide comprising the amino acid sequence of SEQ ID NO:2;
   (iii) an isolated polypeptide consisting of the amino acid sequence set forth in SEQ ID NO:2; and
   (iv) a polypeptide that is encoded by a recombinant polynucleotide comprising the polynucleotide sequence of SEQ ID NO: 1 wherein said host cell comprises an expression system having a nucleic acid which encodes the polypeptide of (i), (ii), (iii), or (iv).

* * * * *

SEQUENCE LISTING

<160> NUMBER OF SEQ ID NOS: 2

<210> SEQ ID NO 1
<211> LENGTH: 1638
<212> TYPE: DNA
<213> ORGANISM: Streptococcus pneumoniae

<400> SEQUENCE: 1

```
atgtcaattt ttattggagg agcatggcca tatgcaaacg gttcgttaca tattggtcac      60
gcggcagcgc ttttaccggg ggatattctt gcaagatact atcgtcagaa gggagaggaa     120
gttttatatg tttctggaag tgattgtaat ggaaccccta tttctatcag agctaaaaaa     180
gaaaataagt ctgtgaaaga aattgctgat ttttatcata aggaatttaa agaaactttt     240
gaaaaattag gttttacata tgacttgtac tcgcgaacag attctccact acatcatgag     300
atagtacaag aattattttt gcaattatac gagaagaaat ttttgtatac aaaaaaaatt     360
aaacaactct attgtacatt tgataatcaa ttcttacctg ataggttcgt tgaaggaaaa     420
tgcccgaatt gtggaaccca ttcaagagga gatcaatgtg ataattgctc agcaatttta     480
gatcctatag atttagttga taaaagatgt tctatttgtt ccaatgaacc agaagttcgt     540
```

-continued

```
gagacagaac acttttatta tgttttagt gagtttcaaa atttgttaga gacttactta    600
aatgatgctg aagaaacagt gagatggcga aaaaatgcaa taaatctaac taaaaggtat    660
ttacgggaag gtttacctga tcgagctgtt actcgtgatc taccaaatgg gattccagtt    720
cccattgatg gttttagaga taaaaaaata tatgtctggt ttgaagcggt agcaggttac    780
tacacagcaa gtgttgattg ggcgcaaaaa cttcaaaata atattactga ttttggaac    840 aatcggacaa agtcatatta tgttcatgga aaagataaca tcccatttca tactattatt    900
tggccggcaa tactctcagg tttagaaata gagcctcttc cagagtatat tatttctagt    960
gaatatttaa cgttagaaaa caaaaaaata tcaacaagta ataattgggc tatatggctt   1020
aacgatatca taaaaaaata tgatgctgat tcaatccgat acttcctaac aataaatgct   1080
cctgagatga aagatgcaaa ttttttcttgg agagaattta tttatagtca taactcagaa   1140
ttattaggat cgtacggtaa ttttatcaat aggactctaa agtttattga aaagtatttt   1200
gaatctgaaa tacccactaa atatctcgaa ggagaaattt tatataattt gaaagaatta   1260
tatacaacag taggtaattt agttgagagc gggcatatga acaggcatt agaagaaatt   1320 tttgaatata ttagatcggc taataaattc tatgatgata tgaaaccgtg gcattgcga    1380 gagtccgata ttgaaaaatg taaagaagtc ttagctactt gtgtaatcat tatacttaat   1440
ttaggacaaa tgttaaatcc attcattcct ttttctggta aaaagattga ggatatgttt   1500
aaaacaaagc taaatacttg gaattatatt tcaaaccttc ctaacaagct atcagatgta   1560
tcaatgttgt tgataggat tgatttgaaa aaaattgacg aggaagtttt agaattgcaa   1620
caaacatcca gtagataa                                                 1638
```

<210> SEQ ID NO 2
<211> LENGTH: 545
<212> TYPE: PRT
<213> ORGANISM: Streptococcus pneumoniae

<400> SEQUENCE: 2

```
Met Ser Ile Phe Ile Gly Gly Ala Trp Pro Tyr Ala Asn Gly Ser Leu
  1               5                  10                  15

His Ile Gly His Ala Ala Leu Leu Pro Gly Asp Ile Leu Ala Arg
                 20                  25                  30

Tyr Tyr Arg Gln Lys Gly Glu Glu Val Leu Tyr Val Ser Gly Ser Asp
         35                  40                  45

Cys Asn Gly Thr Pro Ile Ser Ile Arg Ala Lys Lys Glu Asn Lys Ser
 50                  55                  60

Val Lys Glu Ile Ala Asp Phe Tyr His Lys Glu Phe Lys Glu Thr Phe
 65                  70                  75                  80

Glu Lys Leu Gly Phe Thr Tyr Asp Leu Tyr Ser Arg Thr Asp Ser Pro
                 85                  90                  95

Leu His His Glu Ile Val Gln Glu Leu Phe Leu Gln Leu Tyr Glu Lys
                100                 105                 110

Lys Phe Leu Tyr Thr Lys Lys Ile Lys Gln Leu Tyr Cys Thr Phe Asp
            115                 120                 125

Asn Gln Phe Leu Pro Asp Arg Phe Val Glu Gly Lys Cys Pro Asn Cys
        130                 135                 140

Gly Thr His Ser Arg Gly Asp Gln Cys Asp Asn Cys Ser Ala Ile Leu
145                 150                 155                 160

Asp Pro Ile Asp Leu Val Asp Lys Arg Cys Ser Ile Cys Ser Asn Glu
                165                 170                 175
```

-continued

```
Pro Glu Val Arg Glu Thr Glu His Phe Tyr Tyr Val Phe Ser Glu Phe
            180                 185                 190

Gln Asn Leu Leu Glu Thr Tyr Leu Asn Asp Ala Glu Thr Val Arg
        195                 200                 205

Trp Arg Lys Asn Ala Ile Asn Leu Thr Lys Arg Tyr Leu Arg Glu Gly
    210                 215                 220

Leu Pro Asp Arg Ala Val Thr Arg Asp Leu Pro Asn Gly Ile Pro Val
225                 230                 235                 240

Pro Ile Asp Gly Phe Arg Asp Lys Lys Ile Tyr Val Trp Phe Glu Ala
                245                 250                 255

Val Ala Gly Tyr Tyr Thr Ala Ser Val Asp Trp Ala Gln Lys Leu Gln
            260                 265                 270

Asn Asn Ile Thr Asp Phe Trp Asn Asn Arg Thr Lys Ser Tyr Tyr Val
        275                 280                 285

His Gly Lys Asp Asn Ile Pro Phe His Thr Ile Ile Trp Pro Ala Ile
    290                 295                 300

Leu Ser Gly Leu Glu Ile Glu Pro Leu Pro Glu Tyr Ile Ile Ser Ser
305                 310                 315                 320

Glu Tyr Leu Thr Leu Glu Asn Lys Lys Ile Ser Thr Ser Asn Asn Trp
                325                 330                 335

Ala Ile Trp Leu Asn Asp Ile Ile Lys Lys Tyr Asp Ala Asp Ser Ile
            340                 345                 350

Arg Tyr Phe Leu Thr Ile Asn Ala Pro Glu Met Lys Asp Ala Asn Phe
        355                 360                 365

Ser Trp Arg Glu Phe Ile Tyr Ser His Asn Ser Glu Leu Leu Gly Ser
    370                 375                 380

Tyr Gly Asn Phe Ile Asn Arg Thr Leu Lys Phe Ile Glu Lys Tyr Phe
385                 390                 395                 400

Glu Ser Glu Ile Pro Thr Lys Tyr Leu Glu Gly Glu Ile Leu Tyr Asn
                405                 410                 415

Leu Lys Glu Leu Tyr Thr Thr Val Gly Asn Leu Val Glu Ser Gly His
            420                 425                 430

Met Lys Gln Ala Leu Glu Glu Ile Phe Glu Tyr Ile Arg Ser Ala Asn
        435                 440                 445

Lys Phe Tyr Asp Asp Met Lys Pro Trp Ala Leu Arg Glu Ser Asp Ile
    450                 455                 460

Glu Lys Cys Lys Glu Val Leu Ala Thr Cys Val Ile Ile Leu Asn
465                 470                 475                 480

Leu Gly Gln Met Leu Asn Pro Phe Ile Pro Phe Ser Gly Lys Lys Ile
                485                 490                 495

Glu Asp Met Phe Lys Thr Lys Leu Asn Thr Trp Asn Tyr Ile Ser Asn
            500                 505                 510

Leu Pro Asn Lys Leu Ser Asp Val Ser Met Leu Phe Asp Arg Ile Asp
        515                 520                 525

Leu Lys Lys Ile Asp Glu Glu Val Leu Glu Leu Gln Gln Thr Ser Ser
    530                 535                 540

Arg
545
```